(12) United States Patent
Harmon et al.

(10) Patent No.: US 10,098,892 B2
(45) Date of Patent: Oct. 16, 2018

(54) SOLID DOSAGE FORMULATIONS OF AN OREXIN RECEPTOR ANTAGONIST

(71) Applicant: Merck Sharp & Dohme Corp., Rahway, NJ (US)

(72) Inventors: Paul A. Harmon, Audubon, PA (US); Narayan Variankaval, Plainsboro, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/404,147

(22) PCT Filed: May 29, 2013

(86) PCT No.: PCT/US2013/042959
§ 371 (c)(1),
(2) Date: Nov. 26, 2014

(87) PCT Pub. No.: WO2013/181174
PCT Pub. Date: Dec. 5, 2013

(65) Prior Publication Data
US 2015/0190402 A1    Jul. 9, 2015

Related U.S. Application Data

(60) Provisional application No. 61/653,539, filed on May 31, 2012, provisional application No. 61/787,686, filed on Mar. 15, 2013.

(51) Int. Cl.
| | | |
|---|---|---|
| *A61K 31/551* | (2006.01) | |
| *A61K 9/20* | (2006.01) | |
| *A61K 47/32* | (2006.01) | |
| *A61K 47/38* | (2006.01) | |

(52) U.S. Cl.
CPC .......... *A61K 31/551* (2013.01); *A61K 9/2013* (2013.01); *A61K 9/2018* (2013.01); *A61K 9/2027* (2013.01); *A61K 9/2054* (2013.01); *A61K 47/32* (2013.01); *A61K 47/38* (2013.01)

(58) Field of Classification Search
CPC ....... A61K 31/551; A61K 47/38; A61K 47/32
See application file for complete search history.

(56) References Cited

U.S. PATENT DOCUMENTS

| | | | |
|---|---|---|---|
| 3,222,359 | A | 12/1965 | Reeder et al. |
| 7,780,988 | B2 | 8/2010 | Beyerinck et al. |
| 7,951,797 | B2 | 5/2011 | Breslin et al. |
| 8,026,286 | B2 | 9/2011 | Curatolo et al. |
| 8,030,359 | B2 | 10/2011 | Geers et al. |
| 8,236,328 | B2 | 8/2012 | Babcock et al. |
| 8,703,196 | B2 | 4/2014 | Babcock et al. |
| 9,108,959 | B2 | 8/2015 | Baxter et al. |
| 2007/0178152 | A1 | 8/2007 | Shelton et al. |
| 2008/0132490 | A1 | 6/2008 | Bergman et al. |
| 2009/0124603 | A1 | 5/2009 | Brashear et al. |
| 2009/0187028 | A1 | 7/2009 | Xu et al. |
| 2010/0227903 | A1 | 9/2010 | Geers et al. |
| 2011/0028456 | A1* | 2/2011 | Lulla ............... A61K 9/146 514/220 |
| 2012/0129898 | A1 | 5/2012 | Chatterji et al. |

FOREIGN PATENT DOCUMENTS

| | | |
|---|---|---|
| CN | 103923068 | 7/2014 |
| WO | WO2003000294 A1 | 1/2003 |
| WO | WO2003063821 A2 | 8/2003 |
| WO | WO2007056205 A2 | 5/2007 |
| WO | WO2008069997 | 6/2008 |
| WO | WO2008138755 A3 | 11/2008 |
| WO | WO2012148553 | 11/2012 |
| WO | WO2014072961 | 7/2014 |
| WO | WO2015008218 | 1/2015 |
| WO | WO2015120014 | 8/2015 |
| WO | WO2015164160 | 10/2015 |
| WO | WO2015180060 | 12/2015 |

OTHER PUBLICATIONS

Ash, M. et al., "Copolyvidone", Handbook of Pharmaceutical Additives, (2007), Synapse INformation Resources, Inc., 3rd Ed., p. 1148.*
C. Baxter, et al., "The First Large-Scale Synthesis of MK-4305: A Dual Orexin Receptor Antagonist for the Treatment of Sleep Disorder", Organic Process and Research & Development, 2011, vol. 15(2), pp. 367-375.
Carl R. Hopkins, "ACS Chemical Neuroscience Molecule Spotlight on Suvorexant", ACS Chem. Neuroscience, 2012, vol. 3, 647-648.
C. Cox, et al., "Discovery of the Dual Orexin Receptor Antagonist [(7R)-4-(5-Chloro-1,3-benzoxazol-2-yl)-7-methyl-1, 4diazepan . . . ", J. Med. Chem, 2010, vol. 53, p. 5320-5332.

(Continued)

*Primary Examiner* — Gina C Justice
(74) *Attorney, Agent, or Firm* — J. Eric Thies; John C. Todaro

(57) ABSTRACT

The present invention is directed to a pharmaceutical composition comprising the compound suvorexant, or a pharmaceutically acceptable salt thereof, a concentration-enhancing polymer, and optionally a pharmaceutically acceptable surfactant. The concentration-enhancing polymer is a polymer that forms an amorphous dispersion with suvorexant, that is insoluble or almost completely insoluble in water by (a) dissolving the suvorexant or (b) interacting with the suvorexant in such a way that the suvorexant does not form crystals or crystalline domains in the polymer. A concentration-enhancing polymer is water soluble or readily disperse in water, so that when the polymer is placed in water or an aqueous environment (e.g. fluids in the gastrointestinal (GI) tract or simulated GI fluids), the solubility and/or bioavailability of suvorexant is increased over the solubility or bioavailability in the absence of the polymer.

18 Claims, 5 Drawing Sheets

(56) References Cited

OTHER PUBLICATIONS

EPO European Search Opinion and Supplementary European Search Report for EP2854816 (PCT/US2013/42959), (dated Sep. 29, 2015).
F. Kesisoglou, et al., "Development of an In Vitro-In Vivo Correlation for Amorphous Solid Dispersion Immediate Release Suvorexant Tablets . . . ", J. Pharmaceutical Sciences, 2015, vol. 104, 2913-2922.
P. Kocienski, "Synthesis of Suvorexant", Synfacts, 2011, vol. 8, 822.
P. Kocienski, "Synthesis of Suvorexant", Synfacts, 2012, vol. 8(10), 1049.
I. Mangion, et al., "Enantioselective Synthesis of a Dual Orexin Receptor Antagonist," Org. Letters, 2012, vol. 14(13), 3458-3461.
PCT International Preliminary Report on Patentability for WO2014/072961 (PCT/IB2013/060080) (dated May 12, 2015).
PCT International Search Report for WO2014/072961 (PCT/IB2013/060080) (dated Apr. 3, 2014).
S. Radi, "Suvorexant", Drugs of the Future, 2013, 38(1), 27-36.
N. Strotman, et al., "Reaction Development and Mechanistic Study of a Ruthenium Catalyzed Intramolecular Asymmetric Reductive Amination en Route to the Dual Orexin Inhibitor Suvorexant (MK-4305)", J. Am. Chem. Soc., 2011, vol. 133(21), pp. 8362-8371.
S. Sullivan, "Update on Emerging Drugs for Insomnia", Expert Opin. Emerging Drugs, 2012, vol. 17(3), 295-298.
US Regulatory Label for BELSOMRA® (suvorexant), approved Aug. 13, 2014.
Office Action for China Patent Application 201380028103.2 (PCT/US2013/042959) (dated Dec. 25, 2015).

\* cited by examiner

SOLID DOSAGE FORMULATIONS OF AN OREXIN RECEPTOR ANTAGONIST

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and the scientific literature suggests that they may be involved in various pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinsons disease; Cushings syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

The compound of the formula I:

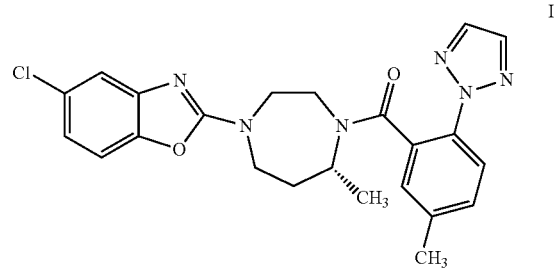 [SMILES: Cc1ccc(-n2nccn2)c(C(=O)N2CCN(c3nc4cc(Cl)ccc4o3)CC[C@H]2C)c1]

5-chloro-2-{(5R)-5-methyl-4-[5-methyl-2-(2H-1,2,3-triazol-2-yl)benzoyl]-1,4-diazepan-1-yl}-1,3-benzoxazole (aka. "suvorexant") is disclosed as an antagonist of orexin receptors in U.S. Pat. No. 7,951,797, US Patent Application Publication US 2008/0132490, PCT Patent Publication WO 2008/069997, Cox et al., J. Med. Chem. 2010, 53, 5320-5332, Strotman et al., JACS, 2011, 133(21), 8362-8371, Baxter et al., Org. Process Res. & Dev., 2011, 15(2) 367-375. This compound may be named as, e.g., "5-chloro-2-{(5R)-5-methyl-4-[5-methyl-2-(2H-1,2,3-triazol-2-yl)benzoyl]-1,4-diazepan-1-yl}-1,3-benzoxazole,""[(R)-4-(5-chloro-benzooxazol-2-yl)-7-methyl-[1,4]diazepan-1-yl]-(5-methyl-2-[1,2,3]triazol-2-yl-phenyl)-methanone" or "[(7R)-4-(5-chloro-1,3-benzoxazol-2-yl)-7-methyl-1,4-diazepan-1-yl][5-methyl-2-(2H-1,2,3-triazol-2-yl)phenyl]methanone."

SUMMARY OF THE INVENTION

The present invention is directed to a pharmaceutical composition comprising the compound suvorexant, or a pharmaceutically acceptable salt thereof, a concentration-enhancing polymer, and optionally a pharmaceutically acceptable surfactant.

DETAILED DESCRIPTION OF THE INVENTION

Figure 1:
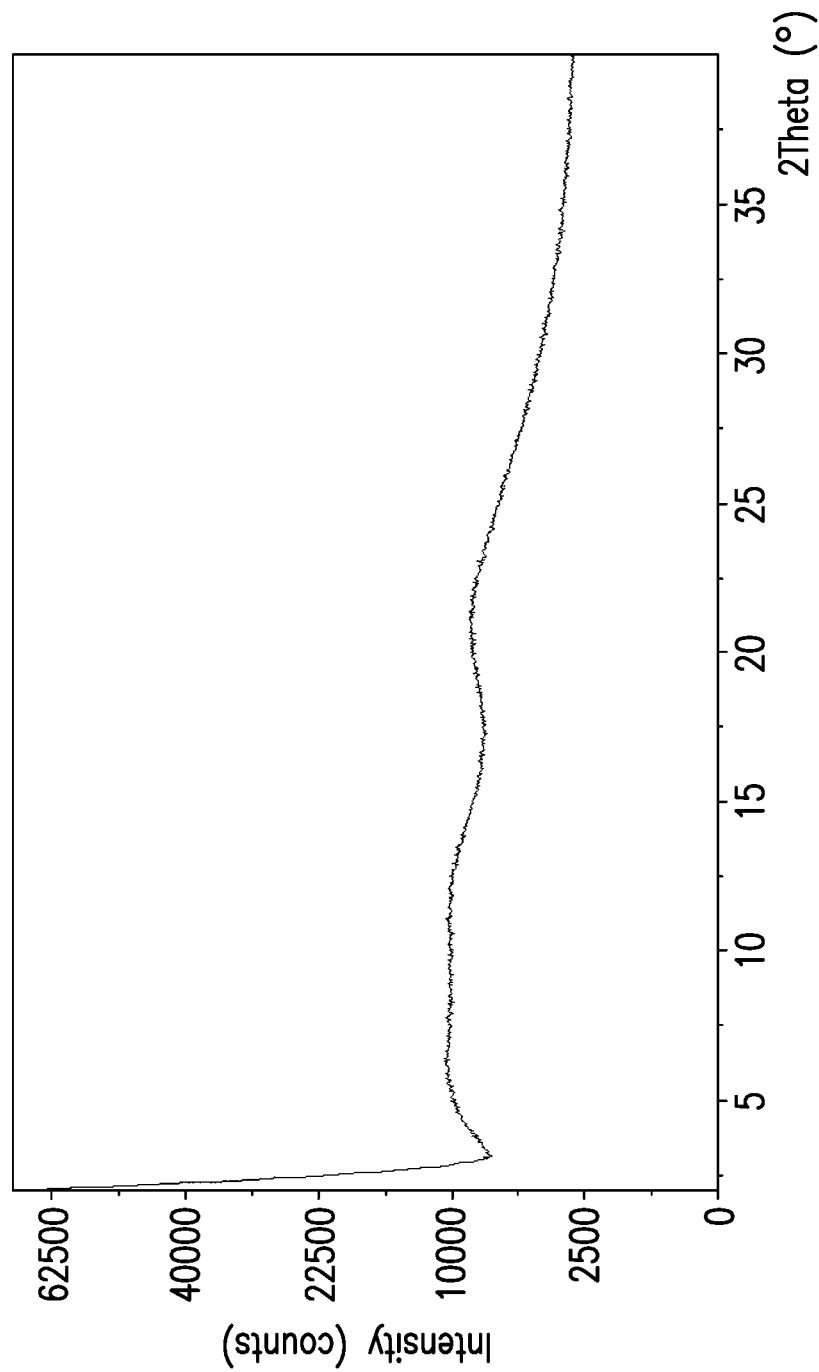
FIG. 1 shows the X-ray powder diffraction (XRPD) pattern of a hot melt extrusion formulation of suvorexant.

The present invention is directed to a pharmaceutical composition comprising:

(1) suvorexant, or a pharmaceutically acceptable salt thereof;

(2) a concentration-enhancing polymer, where the polymer increases the bioavailability of suvorexant, and is water soluble or readily disperses in water; and (3) optionally one or more surfactants.

The concentration-enhancing polymer is a polymer that forms an amorphous dispersion with suvorexant, that is insoluble or almost completely insoluble in water by (a) dissolving the suvorexant or (b) interacting with the suvorexant in such a way that the suvorexant does not form crystals or crystalline domains in the polymer. A concentration-enhancing polymer is water soluble or readily disperse in water, so that when the polymer is placed in water or an aqueous environment (e.g. fluids in the gastrointestinal (GI) tract or simulated GI fluids), the solubility and/or bioavailability of suvorexant is increased over the solubility or bioavailability in the absence of the polymer.

One class of polymers suitable for use with the present invention comprises neutral non-cellulosic polymers. Exemplary polymers include: vinyl polymers and copolymers having substituents that are hydroxy, alkyl, acyloxy, and cyclic amides. These include polyvinyl alcohols that have at least a portion of their repeat units in the unhydrolyzed (vinyl acetate) form (e.g. polyvinyl alcohol-polyvinyl acetate copolymers); polyvinyl pyrrolidinone; polyethylene polyvinyl alcohol copolymers; and polyvinylpyrrolidinone-polyvinyl acetate copolymers. A class of non-cellulosic nonionic polymers comprises polyvinylpyrrolidinone and polyvinylpyrrolidinone copolymers, such as polyvinylpyrrolidinone-polyvinyl acetate copolymers, available as Kollidon polymers and copolymers or Plasdone polymers and copolymers. A representative copolymer is copovidone. These copolymers are often sold under the Kollidon VA64 or Plasdone S630 trademarks. A representative copolymer is polyvinyl caprolactam-polyvinyl acetate-polyethylene glycol graft copolymer. This copolymer is often sold under the Soluplus trademark.

Another class of polymers suitable for use with the present invention comprises ionizable non-cellulosic polymers. Exemplary polymers include: carboxylic acid functionalized vinyl polymers, such as the carboxylic acid functionalized polymethacrylates and carboxylic acid functionalized polyacrylates. This copolymer is often sold under the EUDRAGITS trademark, by Rohm Tech Inc., of Malden, Mass.; amine-functionalized polyacrylates and polymethacrylates; proteins; and carboxylic acid functionalized starches such as starch glycolate.

Concentration enhancing polymers may also be non-cellulosic polymers that are amphiphilic, which are copolymers of a relatively hydrophilic and a relatively hydrophobic monomer. Examples include the acrylate and methacrylate copolymers (EUDRAGITS) mentioned previously. Another example of amphiphilic polymers are block copolymers of ethylene oxide (or glycol) and propylene oxide (or glycol), where the poly(propylene glycol) oligomer units are relatively hydrophobic and the poly(ethylene glycol) units are relatively hydrophilic. These polymers are often sold under the Poloxamer trademark.

A class of polymers comprises ionizable and neutral cellulosic polymers with at least one ester- and/or ether-linked substituent in which the polymer has a degree of substitution of at least 0.1 for each substituent. In the nomenclature used herein, ether-linked substituents are recited prior to "cellulose" as the moiety attached to the cellulose backbone by an ether linkage; for example, "ethylbenzoic acid cellulose" has ethoxybenzoic acid substituents on the cellulose backbone. Analogously, ester-linked substituents are recited after "cellulose" as the carboxylate; for example, "cellulose phthalate" has one carboxylic acid of each phthalate moiety ester-linked to the polymer, with the other carboxylic acid group of the phthalate group remaining as a free carboxylic acid group.

It should also be noted that a polymer name such as "cellulose acetate phthalate" (CAP) refers to any of the family of cellulosic polymers that have acetate and phthalate groups attached via ester linkages to a significant fraction of the cellulosic polymers hydroxyl groups. Generally, the degree of substitution of each substituent group can range from 0.1 to 2.9 as long as the other criteria of the polymer are met. "Degree of substitution " refers to the average number of the three hydroxyls per saccharide repeat unit on the cellulose chain that have been substituted. For example, if all of the hydroxyls on the cellulose chain have been phthalate substituted, the phthalate degree of substitution is 3.

Also included within each polymer family type are cellulosic polymers that have additional substituents added in relatively small amounts that do not substantially alter the performance of the polymer.

Amphiphilic cellulosics may be prepared by substituting the cellulose at any or all of the 3 hydroxyl substituents present on each saccharide repeat unit with at least one relatively hydrophobic substituent. Hydrophobic substituents may be essentially any substituent that, if substituted at a high enough level or degree of substitution, can render the cellulosic polymer essentially aqueous insoluble. Hydrophilic regions of the polymer can be either those portions that are relatively unsubstituted, since the unsubstituted hydroxyls are themselves relatively hydrophilic, or those regions that are substituted with hydrophilic substituents. Examples of hydrophobic substituents include ether-linked alkyl groups such as methyl, ethyl, propyl, butyl, etc.; or ester-linked alkyl groups such as acetate, propionate, butyrate, etc.; and ether- and/or ester-linked aryl-groups such as phenyl, benzoate, or phenylate. Hydrophilic groups include ether- or ester-linked nonionizable groups such as the hydroxyalkyl substituents hydroxyethyl, hydroxypropyl, and the alkyl ether groups such as ethoxyethoxy or methoxyethoxy. Hydrophilic substituents include those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary etherlinked non-ionizable substituents include: alkyl groups, such as methyl, ethyl, propyl, butyl, etc.; hydroxyalkyl groups such as hydroxymethyl, hydroxyethyl, hydroxypropyl, etc.; and aryl groups such as phenyl. Exemplary ester-linked non-ionizable groups include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

An embodiment of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

An embodiment of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid, such as ethoxynicotinic acid, and the various isomers of picolinic acid such as ethoxypicolinic acid, etc.; thiocarboxylic acids, such as 5 thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as aminosalicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer water soluble at least at pH values where any ionizable groups are ionized. In some cases, the aromatic group may itself be ionizable, such as phthalate or trimellitate substituents.

Exemplary cellulosic polymers that are at least partially ionized at physiologically relevant pH's include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary cellulosic polymers that meet the definition of amphiphilic, having hydrophilic and hydrophobic regions include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another subset of cellulosic ionizable polymers are those that possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, and hydroxyethyl cellulose acetate succinate.

As listed above, a wide range of polymers may be used to form amorphous dispersions of suvorexant. In an embodiment of the present invention, the concentration-enhancing polymer comprises a cellulosic polymer that is water soluble in their nonionized state and are also water soluble in their ionized state. A particular subclass of such polymers are the so-called "enteric" polymers, which include, for example, certain grades of hydroxypropyl methyl cellulose acetate phthalate and cellulose acetate trimellitate. Dispersions formed from such polymers generally show large enhancements of the maximum drug concentration in dissolution tests relative to that for a crystalline drug control. In addition, non-enteric grades of such polymers and closely related cellulosic polymers are also useful.

In an embodiment of the present invention, the concentration-enhancing polymer comprises hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate and cellulose acetate isophthalate.

In an embodiment of the present invention, the concentration-enhancing polymer is selected from the group consisting of hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate, cellulose acetate isophthalate, polyvinylpyrrolidinone, vinyl pyrrolidinone/vinyl acetate copolymers, and acrylate and methacrylate copolymers.

In an embodiment of the present invention, the concentration-enhancing polymer is hydroxypropyl methyl cellulose acetate succinate (HPMCAS) or a vinyl pyrrolidinone/vinyl acetate copolymer.

In an embodiment of the present invention, the concentration-enhancing polymer is a pH-insensitive polymer. The term "pH-insensitive polymer" means a polymer that has no appreciable differences in solubility between gastric pH (pH 1-4) and intestinal pH (pH 5-8). Representative pH-insensitive polymers include: vinyl pyrrolidinone/vinyl acetate copolymer, polyvinyl pyrrolidinone/vinyl acetate copolymer, hydroxypropyl methylcellulose, hydroxypropyl cellulose, ethyl cellulose, polyvinyl pyrrolidinone, methacrylate copolymer, polyethylene oxide, polyoxypropylene/polyoxyethylene copolymers (poloxamers), and polyethylene glycol. In an embodiment of the present invention, the concentration-enhancing polymer is vinyl pyrrolidinone/vinyl acetate copolymer or polyvinyl pyrrolidinone/vinyl acetate copolymer.

In an embodiment of the present invention, the concentration-enhancing polymer is a vinyl pyrrolidinone/vinyl acetate copolymer. In an embodiment of the present invention, the concentration-enhancing polymer is polyvinyl pyrrolidinone/vinyl acetate copolymer.

When specific polymers that are suitable for use in the compositions of the present invention are blended, the blends of such polymers may also be suitable. Thus the term "polymer" is intended to include blends of polymers in addition to a single species of polymer.

The pharmaceutical composition of the present invention may optionally comprise one or more surfactants, which may be ionic or nonionic surfactants. The surfactants can increase the rate of dissolution by facilitating wetting, thereby increasing the maximum concentration of dissolved drug. The surfactants may also make the dispersion easier to process. Surfactants may also stabilize the amorphous dispersions by inhibiting crystallization or precipitation of the drug by interacting with the dissolved drug by such mechanisms as complexation, formation of inclusion complexes, formation of micelles, and adsorption to the surface of the solid drug. Suitable surfactants include cationic, anionic, and nonionic surfactants. These include for example fatty acids and alkyl sulfonates; cationic surfactants such as benzalkonium chloride (Hyamine 1622, available from Lonza, Inc., Fairlawn, N.J.); anionic surfactants, such as dioctyl sodium sulfosuccinate (Docusate Sodium, available from Mallinckrodt Spec. Chem., St. Louis, Mo.) and sodium lauryl sulfate (sodium dodecyl sulfate); sorbitan fatty acid esters (SPAN series of surfactants); Vitamin E TPGS; polyoxyethylene sorbitan fatty acid esters (Tween series of surfactants, available from ICI Americas Inc., Wilmington, Del.); polyoxyethylene castor oils and hydrogenated castor oils such as Cremophor RH-40 and Cremopher EL; Liposorb P-20, available from Lipochem Inc., Patterson N.J.; Capmul POE-0, available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides.

The pharmaceutical composition of the present invention may optionally comprise other excipients, such as one or more disintegrants, diluents or lubricants. Representative disintegrants may include croscarmellose sodium, sodium starch glycolate, crospovidone, and starch. Representative glidants may include silicon dioxide and talc. Representative lubricants may include magnesium stearate, stearic acid, and sodium stearyl fumarate. Representative diluents may include microcrystalline cellulose, lactose, and mannitol.

An embodiment of the present invention is directed to a pharmaceutical composition that comprises a concentration-enhancing polymer and 4-40% of suvorexant, or a pharmaceutically acceptable salt thereof. An embodiment of the present invention is directed to a pharmaceutical composition that comprises a concentration-enhancing polymer and 6-20% of suvorexant, or a pharmaceutically acceptable salt thereof. An embodiment of the present invention is directed to a pharmaceutical composition that comprises a concentration-enhancing polymer and 8-15% of suvorexant, or a pharmaceutically acceptable salt thereof. In an embodiment of the present invention, formulations of copovidone with suvorexant and an optional surfactant may comprise 4%-40% suvorexant and 0-10% surfactant, with the balance of the formulation being copovidone. In an embodiment of the present invention, formulations of Kollidon VA64 with suvorexant and an optional surfactant may comprise 4%-40% suvorexant and 0-10% surfactant, with the balance of the formulation being Kollidon VA64. In an embodiment of the present invention, formulations of Plasdone S630 with suvorexant and an optional surfactant may comprise 4%-40% suvorexant and 0-10% surfactant, with the balance of the formulation being Plasdone S630. In an embodiment of the present invention, formulations of Soluplus with suvorexant and an optional surfactant may comprise 4%-40% suvorexant and 0-10% surfactant, with the balance of the formulation being Soluplus. In an embodiment of this invention, formulations of HPMCAS with suvorexant and an optional surfactant may comprise 4%-40% suvorexant and 0-10% surfactant, with the balance of the formulation being HPMCAS.

The pharmaceutical compositions of the present invention are prepared by processes that are suitable for causing a compound (the drug) to form a dispersion (also referred to as an amorphous dispersion) in the polymer such that the drug is generally amorphous or dissolved in the polymer or a component of the composition, such as a surfactant. The dispersions are stable, and the drug does not form crystals or other insoluble particles. Such methods include solution methods, such as spray drying, spray coating, freeze-drying, and evaporation of a co-solvent under vacuum or by heating a solution of polymer and drug. Such methods also include methods that blend the solid drug with the polymer in the molten state, such as hot melt extrusion, and methods of compounding the solid non-molten polymer and drug under heat and pressure to form a dispersion.

Another aspect of the present invention is directed to a process for preparing a composition comprising suvorexant, or a pharmaceutically acceptable salt thereof molecularly dispersed in or dissolved in a concentration-enhancing polymer. In some embodiments it is preferred to select the polymer used in a composition of the invention from those concentration-enhancing polymers providing the following properties: (i) suvorexant is soluble in the polymer; (ii) suvorexant forms a solution or dispersion behaving as a eutectic which has a melting point below the melting point of suvorexant; (iii) when suvorexant is admixed with the selected polymer(s) and heated it apparently acts as a fluxing agent to promote melting the polymer and promote dissolution of suvorexant into the polymer. In some embodiments the process for preparing a composition of the invention comprises: (i) forming a admixture of suvorexant and the selected polymer; (ii) forming a molten dispersion by heating the admixture to a temperature above about 60° C. and below about 200° C., optionally with stirring of the molten dispersion; (iii) cooling the dispersion provided in Step (ii) to form a solid; and (iv) optionally forming a shaped mass from the dispersion either before or contemporaneously with Cooling Step (iii).

Processes for making pharmaceutical compositions of suvorexant with a concentration-enhancing polymer include (a) hot melt extrusion and (b) spray drying. In an embodiment of the present invention, polymers for use in these processes are polyvinylpyrrolidinone, polyvinylpyrrolidinone-polyvinylacetate copolymers (for example copovidone), HPC, HPMCAS, HPMC, HPMCP, CAP, and CAT. In an embodiment of the present invention, polymers for use in hot melt extrusion are polyvinylpyrrolidinone and polyvinylpyrrolidinone-polyvinylacetate copolymers (copovidone such as Kollidon VA64 or Plasdone S630). In an embodiment of the present invention, the polymer for use in hot melt extrusion is copovidone. In an embodiment of the present invention, the polymer for use in hot melt extrusion is Kollidon VA64. In an embodiment of the present invention, the polymer for use in hot melt extrusion is Plasdone S630. In an embodiment of the present invention, the polymer for use in hot melt extrusion is Soluplus. In an embodiment of the present invention, polymers for spray drying include HPC, HPMCAS, HPMC, HPMCP, CAP, and CAT. In an embodiment of the present invention, the polymer for spray drying is HPMCAS.

Both of these processes are well known in the art. In spray drying, the polymer, active compound, and other optional ingredients, such as surfactants, are dissolved in a solvent and are then sprayed through a nozzle as a fine spray into a chamber where the solvent is evaporated quickly to make fine particles comprising polymer, drug, and optional other ingredients. The solvent is any solvent in which all of the components of the composition are soluble and which is readily evaporated in a spray drier. The solvent should also be suitable for use in preparing pharmaceutical compositions. Exemplary solvents are acetone, methanol and ethanol. Methanol and acetone are preferred. In hot melt extrusion, the polymer, drug, and optional surfactants are mixed together in a wet granulation process or other mixing process, and then the mixture of polymer, drug and surfactant are fed into the chamber of an extruder, preferably a twin screw extruder to obtain better mixing, and are then thoroughly melted and mixed to make an amorphous dispersion. In an embodiment of the present invention, chemical or physical foaming of the amorphous dispersion may be employed. Amorphous dispersion that has been subjected to foaming may improve milling performance and provide more rapid dissolution through increased surface area.

In accordance with the present invention, a melt can be prepared in any convenient apparatus in which an admixture of suvorexant and polymer can be heated and optionally stirred. Solidification can be carried out by merely cooling the melt by any means convenient and in any container convenient. Once a solid is obtained, the solid can be further mechanically processed to provide a convenient form for incorporation into a medicament, for example, tablets or capsules.

It will be appreciated that other methods of preparing a melt, solidifying it, and forming the solid into conveniently sized particles can be utilized without departing from the scope of the invention. For example, conveniently, compositions of the invention may be prepared using an extruder. When an extruder is employed to prepare compositions of the invention, conveniently, the material may be introduced into the extruder either in a pre-flux state, that is, as a dry admixture, or in a fluxed state, that is in a melted, plastic, or semi-solid state achieved after the application of sufficient heat to the admixture to cause the suvorexant to dissolve in the polymer, optionally when a fluxed charge is prepared, blending may be employed during heating to promote uniformity of the fluxed material.

If the material is introduced to the extruder in a fluxed state, residence time in the extruder is selected to be just sufficient to insure homogeneity of the composition and the temperature is preferably maintained in the extruder at a level just sufficient to insure that the material maintains its plasticity so that it can be extruded into a conveniently shaped extrudate. If the material is introduced into an extruder in a pre-flux state, the extruder components, for example, the barrels and any mixing chamber present in the equipment, will be maintained at a temperature sufficient to promote fluxing of the admixture. Temperatures selected for use in processing a composition will also take into account that blending which occurs within the extruder equipment, for example, in a mixing section of the barrels, will also contribute to localized fluxing of the admixture by imparting shear-stresses that induce heating in the mixture. Additionally it will be appreciated that equipment temperatures and residence times will be selected to minimize the amount of time that the admixture placed into the extruder spends under conditions of heating and/or shear stress so as to minimize the amount of suvorexant which is decomposed during formation of the composition, as discussed above. In general, extrusion processes in which heating is applied to the material extruded are termed "hot-melt/extrusion processes." When compositions of the present invention are prepared using extruder equipment, the extrudate thus provided can be in any convenient shape, for example, noodles, cylinders, bars, or the like. If desired, the extrudate can be further processed, for example by milling, to provide a particulate form of the composition.

In an alternate embodiment, the present invention is directed to an amorphous form of the compound suvorexant. In an alternate embodiment, the present invention is directed to an isolated amorphous form of the compound suvorexant. In an embodiment of the present invention, the pharmaceutical composition of suvorexant and concentration-enhancing polymer is prepared according to any known process which results in at least a major portion of suvorexant is present in the amorphous state relative to other morphological forms of suvorexant. These processes include mechanical processes, such as milling and extrusion; melt processes, such as high temperature fusion, hot melt extrusion, solvent modified fusion, and melt congealing processes; and solvent processes, including non-solvent precipitation processes, spray coating, and spray-drying. Although the dispersions of the present invention may be made by any of these processes, in an embodiment of the invention suvorexant in the pharmaceutical composition is substantially amorphous and is substantially homogeneously distributed throughout the polymer.

In an alternate embodiment, the present invention is directed to suvorexant in a form which contains at least about 40 wt. % of the amorphous form relative to other morphological forms of suvorexant. In an alternate embodiment, the present invention is directed to suvorexant in a form which contains at least about 50 wt. % of the amorphous form relative to other morphological forms of suvorexant. In an alternate embodiment, the present invention is directed to suvorexant in a form which contains at least about 60 wt. % of the amorphous form relative to other morphological forms of suvorexant. In an alternate embodiment, the present invention is directed to suvorexant in a form which contains at least about 70 wt. % of the amorphous form relative to other morphological forms of suvorexant. In an alternate embodiment, the present invention is directed to suvorexant in a form which contains at least about 80 wt. % of the amorphous form relative to other morphological forms of suvorexant. In an alternate embodiment, the present invention is directed to suvorexant in a form which contains at least about 90 wt. % of the amorphous form relative to other morphological forms of suvorexant. In an alternate embodiment, the present invention is directed to suvorexant in a form which contains at least about 95 wt. % of the amorphous form relative to other morphological forms of suvorexant. In an alternate embodiment, the present invention is directed to suvorexant in a form which contains at least about 98 wt. % of the amorphous form relative to other morphological forms of suvorexant. In an alternate embodiment, the present invention is directed to suvorexant in a form which contains at least about 99 wt. % of the amorphous form relative to other morphological forms of suvorexant. The relative amounts of crystalline and amorphous suvorexant can be determined by several analytical methods, including differential scanning calorimetry (DSC), x-ray powder diffraction (XRPD) and Raman spectroscopy.

The amorphous form of the compound suvorexant was prepared by dissolving a sample of suvorexant in acetone then removing the acetone. In particular, the amorphous form of the compound suvorexant was prepared by dissolving a sample of suvorexant in acetone, heating the solution to 60° C. then removing the acetone on a rotary evaporator. The resultant solid was dried overnight in a vacuum oven at 40° C. to remove any remaining solvent. The thermogram and the diffractogram of the resulting material indicated that it was amorphous.

An embodiment of the present invention is directed to a process for the preparation of an amorphous form of the compound suvorexant which comprises dissolving a sample of suvorexant in acetone then removing the acetone.

The amorphous form of the compound suvorexant may have benefits relative to other morphological forms of suvorexant such as greater solubility and/or a faster dissolution rate than crystalline forms of the compound, which may improve bioavailability of the compound, may facilitate a faster onset of therapeutic action, may reduce variability of therapeutic response among subjects, and may reduce any food effect.

X-ray powder diffraction studies are widely used to characterize molecular structures, crystallinity, and polymorphism. The X-ray powder diffraction patterns were generated on a Philips Analytical XPert PRO X-ray Diffraction System with PW3040/60 console. A PW3373/00 ceramic Cu LEF X-ray tube K-Alpha radiation was used as the source.

DSC data were acquired using TA Instruments DSC 2910 or equivalent instrumentation. A sample with a weight between 2 and 6 mg was weighed into a pan and the pan was crimped. This pan was placed in the sample position in the calorimeter cell. An empty pan was placed in the reference position. The calorimeter cell was closed and a flow of nitrogen is passed through the cell. The heating program was set to heat the sample at a heating rate of 10° C./min to a temperature of approximately 200° C. When the run was completed, the data were analyzed using the DSC analysis program in the system software. The observed endotherms were integrated between baseline temperature points that are above and below the temperature range over which the endotherm is observed. The data reported are the onset temperature, peak temperature and enthalpy.

Raman spectroscopy is widely used to determine the composition and morphological character of samples of interest. FT-Raman (Fourier transform Raman) spectra were collected over the range of 50-4000 cm-1 with a Bruker IFS 66v/S system coupled with the FRA106/S Raman attachment. The signal was averaged for 5-10 minutes at a resolution of 4 cm-1 and a laser power of 300-500 mW. The samples were presented to the laser using a spinning stage which that was rotated during the measurement to provide a large sampling volume.

FIG. 1 shows an X-ray powder diffraction pattern of a hot melt extrusion formulation of suvorexant. The X-ray powder diffraction pattern indicates that the amorphous form of suvorexant is present. The absence of sharp reflections indicate the lack of crystallinity.

Figure 2:
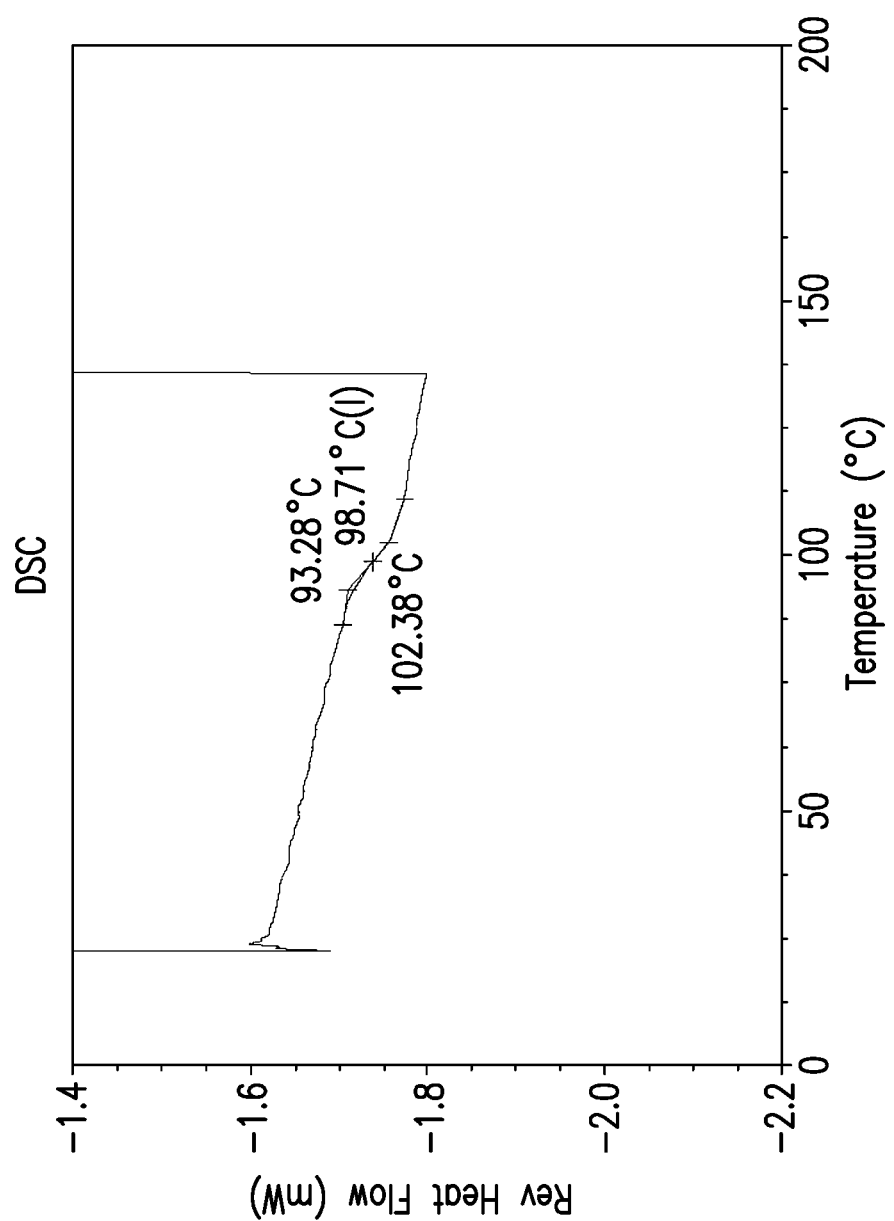
FIG. 2 shows the modulated differential scanning calorimetry (mDSC) thermogram of a hot melt extrusion formulation of suvorexant.

FIG. 2 shows the modulated differential scanning calorimetry (mDSC) thermogram of a hot melt extrusion formulation of suvorexant. As noted by the thermogram, in hot melt extrusion formulations the compound suvorexant is present as an amorphous form that is characterized by a single glass transition temperature. This sample exhibited a single glass transition temperature of approximately 99° C.

Figure 3:
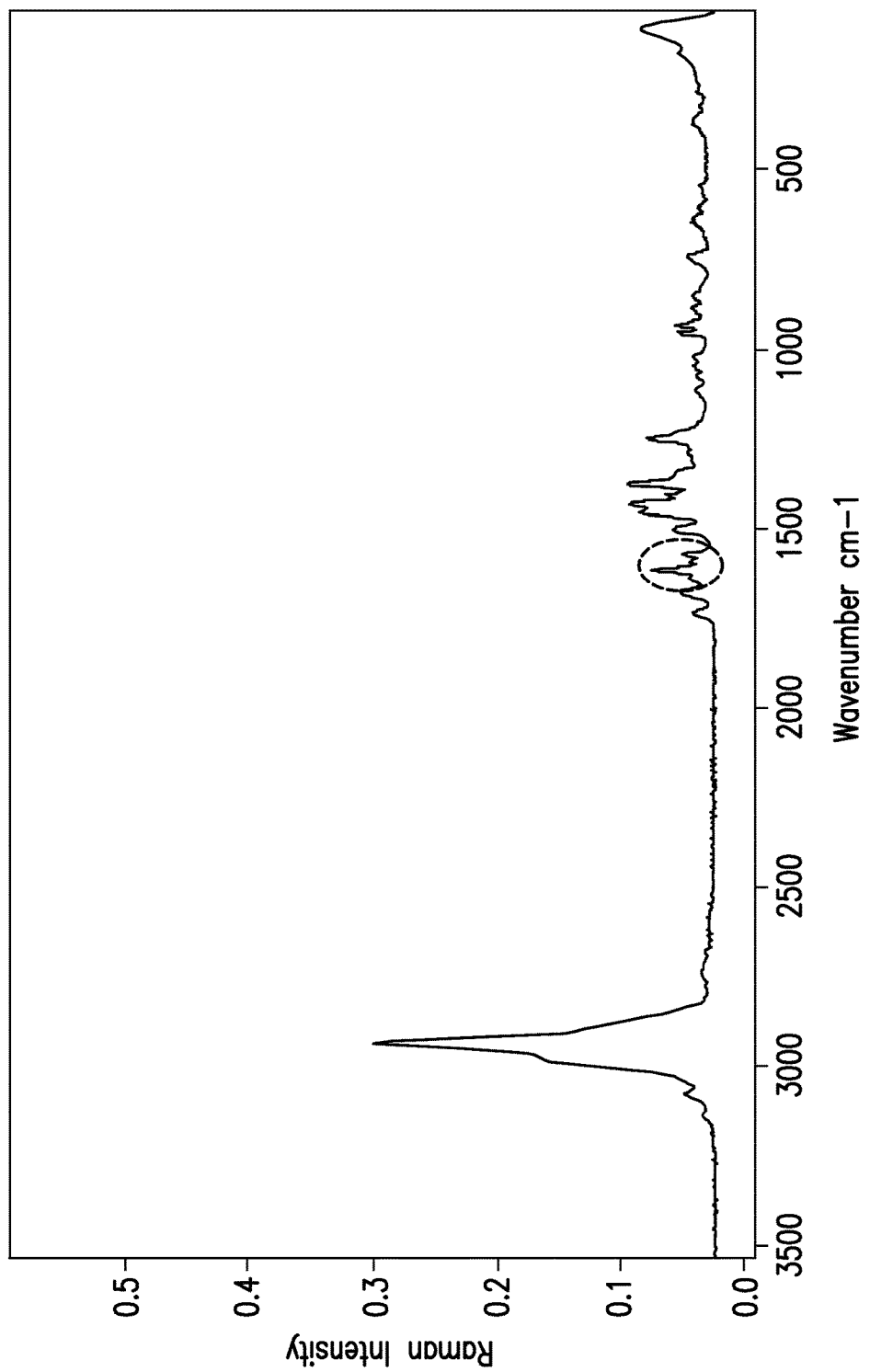
FIG. 3 shows the Raman spectrogram of a hot melt extrudate of suvorexant.

FIG. 3 shows the Raman spectrogram of a hot melt extrudate of suvorexant. As noted by the spectrogram, a hot melt extrudate of suvorexant in the amorphous form is characterized by a Raman spectrogram peak at 1614 cm-1. A hot melt extrudate of suvorexant in the amorphous form is alternatively characterized by a Raman spectrogram peak at 1590 cm-1. A hot melt extrudate of suvorexant in the amorphous form is alternatively characterized by a Raman spectrogram peak at 1571 cm-1.

Figure 4:
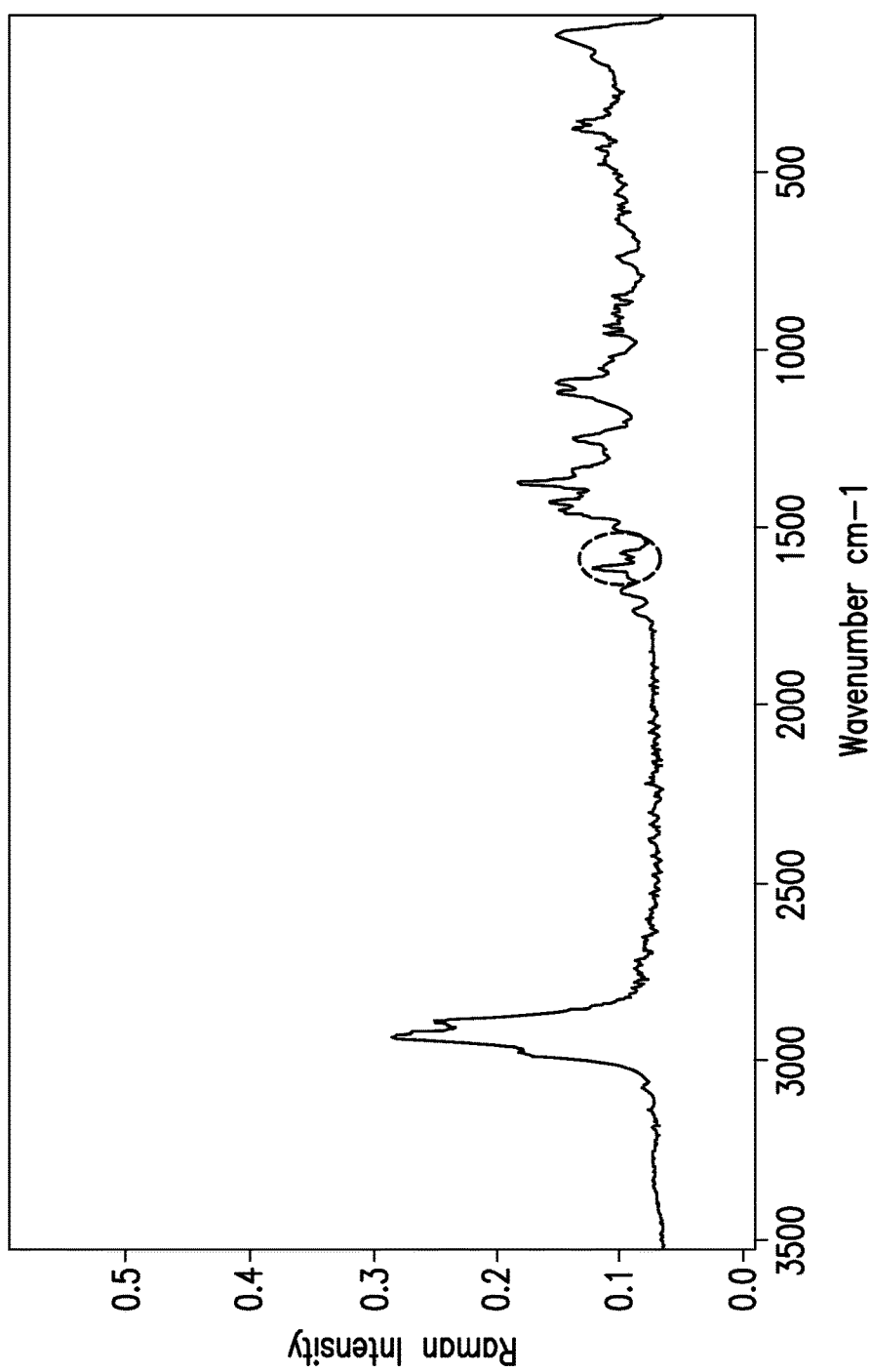
FIG. 4 shows the Raman spectrogram of a tablet formulation that comprises a hot melt extrudate of suvorexant.

FIG. 4 shows the Raman spectrogram of a tablet formulation that comprises a hot melt extrudate of suvorexant. As noted by the spectrogram, a tablet formulation that comprises a hot melt extrudate of suvorexant in the amorphous form is characterized by a Raman spectrogram peak at 1614 cm-1. A tablet formulation that comprises a hot melt extrudate of suvorexant in the amorphous form is alternatively characterized by a Raman spectrogram peak at 1590 cm-1. A tablet formulation that comprises a hot melt extrudate of suvorexant in the amorphous form is alternatively characterized by a Raman spectrogram peak at 1571 cm-1. A tablet formulation that comprises a hot melt extrudate of suvorexant in the amorphous form is alternatively characterized by Raman spectrogram peaks at 1614 cm-1, 1590 cm-1 and 1571 cm-1.

Figure 5:
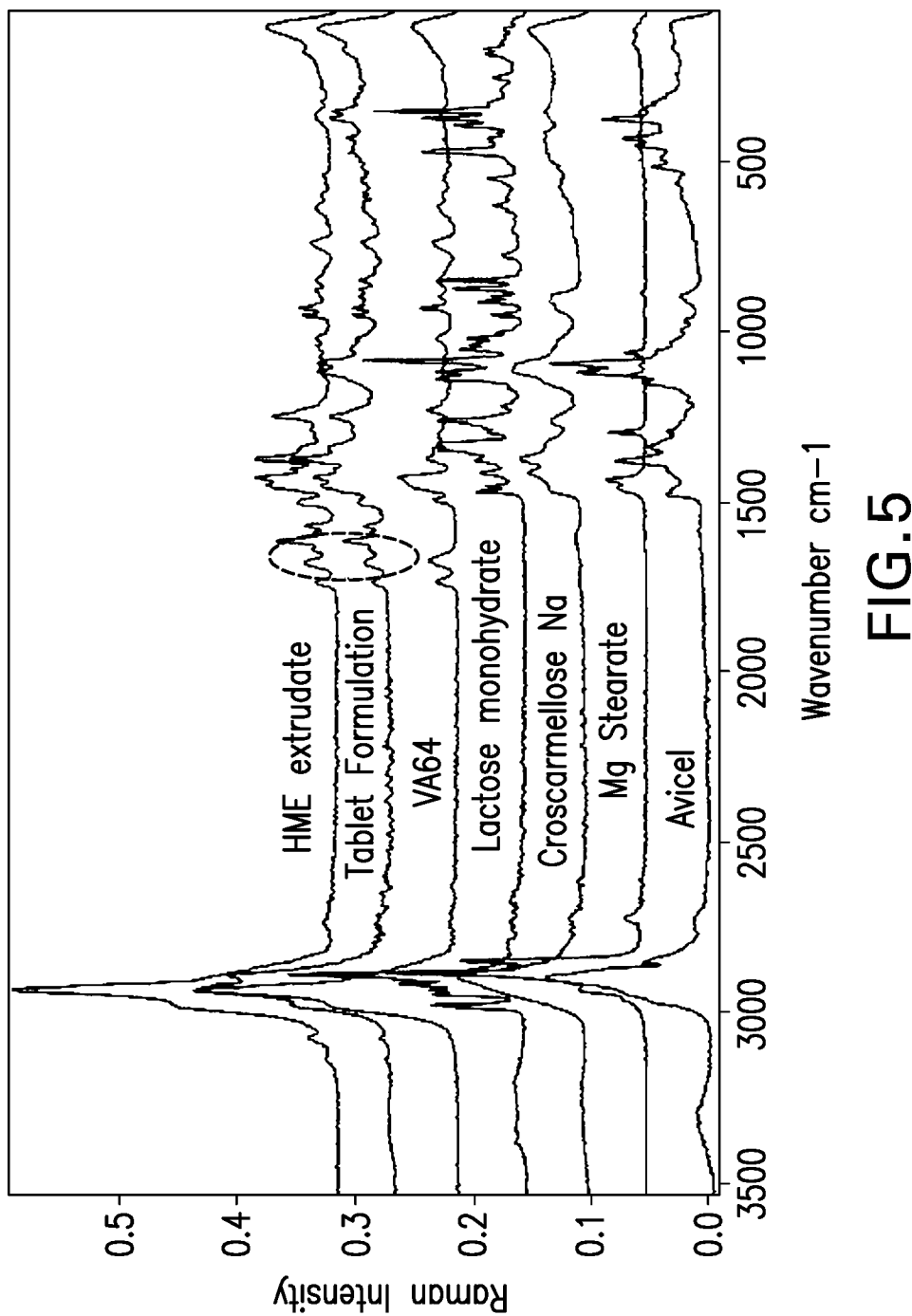
FIG. 5 shows the Raman spectrogram of a hot melt extrudate of suvorexant overlayed with the Raman spectrogram of a tablet formulation that comprises a hot melt extrudate of suvorexant, and further overlayed with the Raman spectrogram of individual excpients in such tablet formulation that comprises a hot melt extrudate of suvorexant.

FIG. 5 shows the Raman spectrogram of a hot melt extrudate of suvorexant overlayed with the Raman spectrogram of a tablet formulation that comprises a hot melt extrudate of suvorexant, and further overlayed with the Raman spectrogram of individual excpients in such tablet formulation that comprises a hot melt extrudate of suvorexant.

Suvorexant is disclosed as having activity in antagonizing the human orexin-1 (OX1) receptor with a Ki of 0.55 nM and in antagonizing the human orexin-2 (OX2) receptor with a Ki of 0.35 nM. Relative to standard pharmaceutical formulations of suvorexant, the present invention may have benefits such as providing greater solubility of suvorexant and/or a faster dissolution rate than standard formulations of the compound, which may improve bioavailability of the compound, may facilitate a faster onset of therapeutic action, may reduce variability of therapeutic response among subjects, and may reduce any food effect.

The compositions comprising the concentration-enhancing polymer increase the concentration of suvorexant in an aqueous environment, such as water, the gastrointestinal (GI) tract, or a simulated GI fluid prepared for in vitro laboratory tests relative to a control composition comprising an equivalent amount of suvorexant without polymer. Once the composition is introduced into an aqueous environment, the composition comprising the concentration-enhancing polymer and suvorexant provides a higher maximum aqueous concentration of suvorexant relative to a control composition having the same concentration of suvorexant but without the concentration-enhancing polymer. An inert filler may be used in place of the polymer in the control to keep the suvorexant at the same concentration as in the composition comprising the polymer. In an embodiment of the present invention, the polymer increases the maximum concentration of suvorexant in an aqueous solution by at least 25%. In an embodiment of the present invention, the polymer increases the maximum concentration of suvorexant in an aqueous solution by at least 50%. In an embodiment of the present invention, the polymer increases the maximum concentration of suvorexant in an aqueous solution to at least double relative to a control composition. In an embodiment of the present invention, the polymer increases the maximum concentration of suvorexant in an aqueous solution to at least 5-times greater that than that of a control composition. In an embodiment of the present invention, the polymer increases the maximum concentration of suvorexant in an aqueous solution by at least 10-fold. Such large enhancements in concentration may be necessary in order for suvorexant to achieve effective blood levels through oral dosing. Such aqueous solutions are generally supersaturated solutions with respect to suvorexant.

In in vivo pharmacokinetics measurements in which the concentration of suvorexant is measured as a function of time in blood or serum after administration of the formulation to a test animal, the compositions of the present invention exhibit an area under the concentration versus time curve (AUC) and a maximum concentration Cmax that is greater than that of a control composition comprising an equivalent quantity of the compound without the concentration-enhancing polymer. In an embodiment of the present invention, the area under the concentration versus time curve (AUC) is at least 25% greater than that of a control composition. In an embodiment of the present invention, the AUC is at least 50% greater than that of a control composition containing the same amount of drug but without the polymer. In an embodiment of the present invention, the area under the AUC is at least double than that of a control composition containing the same amount of drug but without the polymer. In an embodiment of the present invention, the area under the AUC is at least 5-times greater than that of a control composition containing the same amount of drug but without the polymer. In an embodiment of the present invention, the area under the AUC is at least 10-fold greater than that of a control composition containing the same amount of drug but without the polymer. In an embodiment of the present invention, the area under the AUC is at least 15-fold greater than that of a control composition containing the same amount of drug but without the polymer. In an embodiment of the present invention, the area under the AUC is at least 20-fold greater than that of a control composition containing the same amount of drug but without the polymer.

In an embodiment of the present invention, the Cmax is increased by at least 25% relative to a control composition without the concentration-enhancing polymer after it is administered to a test animal or patient. In an embodiment of the present invention, the Cmax is increased by at least 50% relative to a control composition without the polymer after it is administered to a test animal or patient. In an embodiment of the present invention, the Cmax is increased by at least double relative to a control composition without the polymer after it is administered to a test animal or patient. In an embodiment of the present invention, the Cmax is also increased by at least 5-times greater that than that of a control composition without the polymer after it is administered to a test animal or patient. In an embodiment of the present invention, the Cmax is also increased by at least 10 times greater than the drug concentration of a control composition without the polymer after it is administered to a test animal or patient. In an embodiment of the present invention, the Cmax is also increased by at least 20 times greater than the drug concentration of a control composition without the polymer after it is administered to a test animal or patient. In an embodiment of the present invention, the Cmax is also increased by at least 30 times greater than the drug concentration of a control composition without the polymer after it is administered to a test animal or patient. In an embodiment of the present invention, the Cmax is also increased by at least 40 times greater than the drug concentration of a control composition without the polymer after it is administered to a test animal or patient.

The pharmaceutical compositions of the present invention exhibit improved in vivo bioavailability compared with formulations that do not have the concentration-enhancing polymer. The compound suvorexant is absorbed more rapidly after oral administration of these formulations. The AUC of the drug and the maximal concentration of the drug in the blood or serum are increased when the formulations are administered to a patient.

In in vivo pharmacokinetics measurements in which the concentration of suvorexant is measured as a function of time in blood or serum after administration of the formulation to a test animal or human patient upon co-administration with food (such as a high fat meal), the compositions of the present invention that employ a concentration-enhancing polymer that is a pH-insensitive polymer may exhibit a time to peak concentration (Tmax) that is shorter than that of a composition comprising an equivalent quantity of the compound that employ a concentration-enhancing polymer that is not a pH-insensitive polymer. Accordingly, the use of a concentration-enhancing polymer that is a pH-insensitive polymer may help to reduce the food effect that otherwise delays the Tmax when a formulation of suvorexant is administered with food (such as a high fat meal).

Oral administration of a pharmaceutical composition of the present invention surprisingly reduces the food effect, that is, oral administration of a formulation comprising a composition of the invention provides substantially the same suvorexant exposure and less variability in bioavailability across a patient population regardless of whether the formulation is administered under Fed Conditions or Fasted Conditions. Moreover, when the results of oral administration of a formulation comprising a composition of the invention are compared to those obtained after administration of an equivalent amount of suvorexant in the form of a conventional formulation, under either fed conditions or fasted conditions, the composition of the invention yields increased bioavailability, with lower variability in bioavailability across a population of subjects, and higher exposure levels (AUC) in healthy volunteers to whom it is administered. Moreover, it is believed that similar results are achieved in patients to whom formulation comprising a composition of the invention is administered.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound employed in the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to suvorexant are meant to also include the pharmaceutically acceptable salts.

Exemplifying the invention is the use of the formulations disclosed in the Examples and herein. Suvorexant or a pharmaceutically acceptable salt thereof is useful in a method of antagonizing orexin receptor activity in a patient such as a mammal in need of such inhibition comprising the administration of an effective amount of the compound. The present invention is directed to the use of the formulations of suvorexant or a pharmaceutically acceptable salt thereof as antagonists of orexin receptor activity. In addition to primates, especially humans, it is possible that a variety of other mammals may be treated according to the method of the present invention.

The subject treated in the present methods is generally a mammal, such as a human being, male or female. The term therapeutically effective amount means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment "and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The scientific literature has implicated the orexin receptors in a wide range of biological functions. This has suggested a potential role for these receptors in a variety of disease processes in humans or other species. In accordance with the present invention, the formulations of suvorexant or a pharmaceutically acceptable salt thereof may have utility in treating, preventing, ameliorating, controlling or reducing the risk of neurological and psychiatric disorders associated with orexin receptors. In accordance with the present invention, the formulations of suvorexant or a pharmaceutically acceptable salt thereof may provide methods for: preventing and treating sleep disorders and sleep disturbances; treating insomnia; enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; in a mammalian patient in need thereof which comprises administering to the patient a therapeutically effective amount of suvorexant or a pharmaceutically acceptable salt thereof in a formulation of the present invention.

In accordance with the present invention, the formulations of suvorexant or a pharmaceutically acceptable salt thereof may also be useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patients weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 15 mg, 20 mg, 25 mg, 30 mg, 40 mg, 50 mg, or 100 mg active ingredient. In specific embodiments, the pharmaceutical composition may be provided in a solid dosage formulation comprising about 10 mg, 15 mg, 20 mg, 30 mg, or 40 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compound may be administered on a regimen of 1 to 4 times per day, such as once or twice per day. In an embodiment of the present invention, the compound may be administered in a regimen of once per day in the evening, such as prior to initiating sleep.

Suvorexant or a pharmaceutically acceptable salt thereof that is employed in the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, suvorexant or a pharmaceutically acceptable salt thereof that is employed in the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When suvorexant or a pharmaceutically acceptable salt thereof is used contemporaneously with one or more other drugs, a pharmaceutical composition containing such other drugs in addition to the compound of the present invention is contemplated. Such pharmaceutical compositions are prepared without undue experimentation in accordance with the methods described herein and known in the art. Accordingly, the pharmaceutical compositions of the present invention include those that also contain one or more other active ingredients, in addition to a compound of the present invention.

The weight ratio of suvorexant or a pharmaceutically acceptable salt thereof to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The pharmaceutical compositions of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared in accordance with the methods described herein and other method known to the art for the manufacture of pharmaceutical compositions. Such compositions may further contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Dispersible powders and granules suitable for preparation of an aqueous suspension by the addition of water provide the active ingredient in admixture with a dispersing or wetting agent, suspending agent and one or more preservatives.

Several methods for preparing the pharmaceutical formulations of this invention are illustrated in the following Examples. In some cases the order of carrying out the foregoing examples may be varied to facilitate the efficiency of the process or desired properties of the formulation. The following examples are provided so that the invention might be more fully understood. These examples are illustrative only and should not be construed as limiting the invention in any way.

EXAMPLES

Examples of preparations of pharmaceutical formulations are provided below. Bioavailability is determined in vivo by dosing trial formulations and/or other formulations of suvorexant to Beagle dogs at a dose of 5 mg/kg of suvorexant and then measuring the amount of suvorexant in the serum or blood as a function of time. Comparisons are made with other formulations containing the same amount and same concentration of suvorexant, such as a solid formulation with conventional excipients. Dissolution of the formulations in water or simulated gastric fluid can be observed and measured to determine the concentration and rate of dissolution of suvorexant in the fluid using the formulations of this invention or other formulations, including formulations with conventional excipients as controls to determine the improvements in dissolution using the formulations of this invention.

Example 1

Preparation of Spray Dry Formulations

Formulation 1:
Spray dried formulations comprised: suvorexant (10-20% w/w); an optional surfactant, such as (1) 2-4% SDS (sodium dodecyl sulfate), (2) 2.5% Vitamin E TPGS, (3) 2% Tween 80, (4) 2% Span 80, or (5) 2% Cremophor EL, or a mixture of two or more of these surfactants; and the balance is either HPMCAS-L, HPMCAS-M, or HPMCAS-H (purchased as AQOAT from Shin Etsu). The components were dissolved or suspended in a solvent system, such as acetone, methanol, and mixtures of organic solvents with water (0.5-18% w/v solids), and then spray dried as described below.

Solution Preparation:
Suvorexant, optional surfactant or surfactants, and polymer were mixed with acetone, methanol, or mixtures of organic solvents with water as follows, yielding a solution (which may be a structured suspension). The drug, surfactant, and polymer were dissolved in the solvent. The polymer was slow to dissolve and was added to the solvent over an extended period of time with vigorous stirring, such as by using an impeller or magnetic stir bar and stir plate. The resulting solution/suspension was stirred for at least an additional 60 min prior to spray drying.

Spray Drying Process 1:
Spray drying was carried out in a Niro SD Micro spray drier. Heated dry nitrogen and formulation solution were fed concurrently into a two-fluid nozzle and then discharged as a spray into the drying chamber, along with additional heated gas, resulting in rapid evaporation to form particles. The dried particles were carried by the processing gas into a cyclone and then into a bag filter chamber for collection. Three processing rates were controlled and monitored: 1) solution feed rate, 2) processing nitrogen flow rate, and 3) atomizing nitrogen flow rate. The solution feed rate was controlled by an external peristaltic pump, and is ~5-20 ml/min on a laboratory scale. The atomizing nitrogen rate and processing nitrogen rates were 2-3 kg/hr for atomizing nitrogen and 20-30 kg/hr for processing nitrogen. The targeted processing gas temperature at the drying chamber outlet was slightly below the boiling point of the solvent system, although temperatures in the range of 30 to 70° C. were demonstrated to be adequate, and the inlet chamber temperature (at the outlet of the nozzle) was adjusted to obtain the desired outlet temperature. An inlet temperature set point of 80-90° C. was typical. Residual solvent levels in the product was typically low (<1% w/w).

Spray Drying Process 2
The processing configuration was similar to Process 1, except that spray drying was carried out in a Niro PSD-1 extended chamber spray drier equipped with a two-fluid nozzle with 1 mm orifice. The following processing conditions were controlled or monitored: formulation solution feed rate (2-7.6 kg/hr), processing gas flow rate (35-38 mm $H_2O$), atomization ratio (ratio of atomization gas flow rate to feed rate) (0.9-2.8), atomization pressure (0.25-1.5 bar), outlet gas temperature (43-70° C.), and inlet gas temperature (61-134° C.)

Post Spray Drying Processing:
At the smaller processing scale, material collection occurred in two areas, the cyclone and the bag filter chambers. Typical mean particle sizes resulting from the Spray Drying Process 1 ranged from 1 to 30 μm, with individual particles measuring between <1 μm and >100 m, as sampled from the cyclone collection area. The majority of particles in the bag filter were 1 μm or less, although the particles were highly agglomerated. Under Spray Drying Process 2 conditions, particles were harvested from the cyclone collection chamber only, and the typical mean particle size may be much larger, typically ranging between 5 to 70 μm.

The spray dried particles were made into granules as follows. The particles were blended in a suitable blender (V or Bohle) with microcrystalline cellulose such as Avicel (a filler), lactose (a filler), croscarmellose sodium (a disintegrant), colloidal silicon dioxide (a glidant), and magnesium stearate (a lubricant). The blended powders were then roller compacted into granules, subjected to extragranular lubrication, and filled into capsules.

A formulation prepared as described above that comprised of 10% (w/w) suvorexant, 40% HPMCAS-LF, 42.5% lactose monohydrate, 6% croscarmellose sodium, 0.5% colloidal silicon dioxide, and 1% magnesium stearate was transferred to capsules, with each capsule containing 50 mg of suvorexant. The pharmacokinetic profile of this composition was tested in a panel of 3 fasted beagle dogs with a single dose of 1 mg/kg. The pharmacokinetic measurements of suvorexant in the blood for a period of 24 hours was as follows: $AUC_{0-24}$ is 52.3±19.1 µM*hr; $C_{max}$ is 6.95µ2.23 µM; and $T_{max}$ is 1.0 hr with a range of 1.0-2.0 hr.

For comparison, a formulation containing suvorexant without the polymer or spray drying process was made and tested, as follows. The non-polymer formulation contained 25% of suvorexant, 3% croscarmellose sodium, 1% magnesium stearate 35.5% microcrystalline cellulose, and 35.5% lactose, and was prepared by roller compaction and compressed into a tablet. The pharmacokinetic profile of this composition was measured by administering a single 5 mg/kg dose to a panel of 3 fasted beagle dogs and then measuring the amount of suvorexant in the blood of the dogs for a period of at least 24 hours. The pharmacokinetic data was as follows: $AUC_{0-24}$ is 3.04±1.40 µM*hr, $C_{max}$ is 0.34±0.10 µM, and $T_{max}$ is 2.0 hr with a range of 1.0-2.0 hr. The pharmacokinetics are not as good for the conventional formulation as for the polymer formulations.

Example 2

Preparation of Hot Melt Extrusion Formulations

The following two formulations were made by hot melt extrusion. Amounts are expressed as weight %. KollidonVA64 is a copolymer of polyvinylpyrrolidinone and polyvinyl acetate having a co-monomer ratio of about 1.2:1. It is also known as copovidone. It has a glass transition temperature (Tg) of about 110° C.
(1) suvorexant, 20%; Kollidon VA64, 80%.
(2) suvorexant, 20%; HPMCAS-LG, 80%
Formulation 1

Formulation 1 was made by blending the two components, and then feeding the mixture into a twin screw extruder. The mixture was made by combining the KollidonVA64 polymer and suvorexant at room temperature in a Bohle bin blender equipped with a 2 liter bin.

The pre-extrusion blend was fed into a Thermo Prism 16 mm L/D 40:1 Hot Melt Twin Screw Extruder. The barrel of the extruder had 10 temperature zones numbered 1-10, with Zone 1 at the entry end of the barrel and Zone 10 just before the die. Zone 1 was not heated and has no temperature measurement. Zones 2-10 each have temperature control, and the temperatures of each of these zones were measured. The temperature of the die was not controlled but can be measured. The feed was introduced into Zone 2 through a feed throat. The screws were designed so that mixing occurred across Zones 4 and 5. The mixing ended immediately past the vent port. The pre-extrusion mixture was fed into the feed port of the extruder at about 10 g/min from a K-Tron twin-screw gravimetric feeder. The screw speed was 100 rpm. The profile of temperature set points in the extruder for Zones 2-10 was: Zones 2-5, 20° C.; Zones 6-10, 130° C. The actual temperatures in these zones were: Zone 2, 22-23° C.; Zone 4, 80° C.; Zones 6-10, 180° C. Zone 10 was initially set at 190° C. to avoid pressure during startup, and then the temperature set point was lowered to 180° C. once the extrusion began. The temperature of the molten product exiting from the die was 200° C. There was no appreciable buildup of die pressure. The extrudate was clear, and it appeared homogeneous. The solid extruded polymer was then milled using a Fitz Mill with a knife configuration, Impact forward, with a 1722-0033 screen at 7500 rpm.

In an alternate procedure, a formulation was made by blending the two components, and then feeding the mixture into a twin screw extruder. The mixture was made by combining the copovidone polymer and suvorexant at room temperature in a bin blender. The pre-extrusion blend was fed into a 40/1 L/D twin screw extruder. The extruder had 12 temperature zones numbered 1-12, with Zone 1 at the entry end of the barrel and Zone 10 the end of the barrel sections with zone 11 being an adaptor to change the flow regime to a single orifice and zone 12 being a die adaptor. Zone 1 was maintained at low temperatures by cooling water. Zones 2-12 each have temperature control, and the temperatures of each of these zones were measured. The feed was introduced into Zone 2 through a side stuffer. The screws were designed so that a melt seal was formed at zone 3 allowing moisture venting at zone 4. Mixing occurred across Zones 6 and 7 allowing further moisture venting at zone 8. The pre-extrusion mixture was fed into the feed port of the extruder from a twin-screw gravimetric feeder. The screw speed was 300 rpm. The profile of temperature set points in the extruder for Zones 2-12 was: Zone 2, 42° C.; Zone 3, 100° C.; zone 4, 130° C. Zones 5-12, 180° C. The temperature of the molten product exiting from the die was 185° C. There was no appreciable build-up of die pressure. The extrudate was clear, and it appeared homogeneous. The extruded material was fed through counter rotating rolls chilled to 10-12° C. to bring the melt below its glass transition temperature and form a brittle glass sheet, that was conveyed to a coarse mill, and broken up into small pieces. The extrudate was then further milled using an impact mill with a hammer configuration with a 0.84 mm screen at mill tip speed of 40-45 m/s.
Formulation 2

Formulation 2 was made using the same procedure as was used for Formulation 1. The extrusion was carried out under the same general conditions as the extrusion of Formulation 1. The only change was that the temperature of Zones 6-10 was set to 140° C. and Zone 10 was initially set at 150° C., before lowering back to 140° C. The temperature of the molten extrudate as it exited from the die was 140° C. The die pressure was low. The extrudate was milled using the same method as was used for Formulation 1.

Example 3

Preparation of Tablet Formulations by Hot Melt Extrusion

The formulation composition for making tablets containing 8% of suvorexant are shown in the following table. In accordance with the present invention, the compositions can be varied more broadly.

| Component | Composition (% w/w) |
| --- | --- |
| Suvorexant | 8% |
| Copovidone | 32% |
| Lactose monohydrate | 16.5% |
| Microcrystalline cellulose | 33% |
| Croscarmellose sodium | 10% |
| Magnesium stearate | 0.5% |

Representative ranges of the amounts of the components that can be used and their function are as follows: suvorexant (API), 0.5-40%; 5-30% copovidone (stabilizing polymer), 0.25-40%; microcrystalline cellulose (filler), 5-95%; lactose (filler), 5-95%; croscarmellose sodium (disintegrant), 1-10%; magnesium stearate (lubricant). Representative ranges of the amounts of suvorexant and copovidone are 1-40% and 5-90%, respectively.

In an embodiment of the present invention, substitutes may be used in place of the polymers and excipients. For example, where a trade name or brand name is used, the same materials having other brand or trade names may also be used: stabilizing polymer—Eudragits (acrylate-methacrylate copolymers), PVP, HPC, HPMC, HPMCP, HPMCAS, CAS, CAP, and CAT; Surfactants—SDS, Cremophor (various grades), polysorbates (various grades), Solutol, Gelucires, Spans (various grades), PEGs; fillers—dicalcium phosphate, silicified microcrystalline cellulose, starch, mannitol; disintegrants—crospovidone, sodium starch glycolate, calcium silicate, starch; optional colorants—red iron oxide, yellow iron oxide, black iron oxide, titanium dioxide, FD&C Blue #2; and optional coating—Opadry I, Opadry II, Opadry II HP.

| Unit Strength = 10 mg | |
|---|---|
| Component | mg/tablet |
| Suvorexant | 10 |
| Polyvinylpyrrolidone/Vinyl Acetate Copolymer (Kollidon VA64) | 40 |
| Lactose monohydrate (316 Fast-Flo) | 20.625 |
| Microcrystalline cellulose (Avicel PH102) | 41.25 |
| Croscarmellose sodium | 12.5 |
| Magnesium stearate | 0.625 |
| (Core Tablet Weight | 125 mg) |

| Unit Strength = 30 mg | |
|---|---|
| Component | mg/tablet |
| Suvorexant | 30 |
| Polyvinylpyrrolidone/Vinyl Acetate Copolymer (Kollidon VA64) | 120 |
| Lactose monohydrate (316 Fast-Flo) | 61.875 |
| Microcrystalline cellulose (Avicel PH102) | 123.75 |
| Croscarmellose sodium | 37.5 |
| Magnesium stearate | 1.875 |
| (Core Tablet Weight | 375 mg) |

The formulations in the table above were made by hot melt extrusion by the following procedure. Suvorexant was fed using a Ktron K20 twin screw powder feeder at extruder barrel zone 1 through the top feed port of the barrel section (2 kg/hr). Polymer (Kollidon VA64) was fed using a Ktron K20 twin screw powder feeder at extruder barrel zone 2 through a twin screw Leistritz side stuffer with top vent port in the barrel section (8 Kg/hr).

A vent (or two vents) were located at barrel zones 7, 8, and/or 9. These were ambiently vented to remove water vapor. The remaining barrel sections were closed. All feeders are placed on load cells to continuously monitor changes in weight. The barrel temperature was at room temperature at zone 1, and the temperatures were at about 130° C. at Zone 3 or 4. Zones 5-10 were heated to about 180° C.

A four hole strand die was used to extrude material onto a chilled roll unit made by ThermoElectron. The chilled roll unit used cool water to produce a brittle sheet of extrudate that was subsequently chopped up into particles by a "kibbler" (basically a rotor with perpendicular pegs that wacks at the brittle sheet that is conveyed to the rotor).

The particles from the kibbler above were milled using a Fitz mill prior to downstream processing/tabletting. The milled extrudate was then blended in a suitable blender (V or Tote) with microcrystalline cellulose (e.g. Avicel) (a filler), lactose (a filler), and croscarmellose sodium (a disintegrant). The blend was then lubricated with magnesium stearate. The lubricated blend is compressed into tablets. The compressed tablets may optionally be coated.

The pharmacokinetic profile of this composition of suvorexant was tested by administering a single dose of the formulation at a dose of 5 mg/kg to panels of 3 fasted beagle dogs and measuring the concentration of suvorexant in the blood for a period of at least 24 hours. The pharmacokinetic measurements of suvorexant were as follows: $AUC_{0-24}$ (µM-hr) 2.82±0.493; Cmax (µM) 0.587±0.182; Tmax (hr) 1.0 (0.5-2.0).

The pharmacokinetic profile of this composition of suvorexant was also tested by administering a single dose of the formulation to healthy human men. In this study, this composition of suvorexant helped to reduce the food effect when a formulation of suvorexant is administered with food (such as a high fat meal). In the first treatment period of this clinical study, a single, oral dose of this composition of suvorexant (40 mg) was administered to 7 subjects in a fasted state (following an 8-hour fast), and a single, oral dose of this composition of suvorexant (40 mg) was administered to 7 different subjects following a standard high-fat breakfast. In the second period of this clinical study, the 7 subjects in each treatment groups were crossed over and received the other treatment.

As shown in the following table, $AUC_{0-\infty}$ and $C_{max}$ for this composition of suvorexant remained unchanged after administration with a high fat breakfast compared to administration in a fasted state. The fed/fasted GMR and 90% confidence intervals for $AUC_{0-inf}$ were 0.98 (0.90, 1.07). The fed/fasted GMR and 90% confidence intervals for $C_{max}$ were 1.09 (0.90, 1.33). Median $T_{max}$ was 3.0 hours after a high fat breakfast and 2.0 hours in a fasted state. Mean apparent terminal $t_{1/2}$ when administered after a high fat breakfast was largely unchanged compared to administration in a fasted state, with $t_{1/2}$ values of 11.8 and 10.9 hours respectively.

| Pharmacokinetic Parameter | Suvorexant Fasted | | | Suvorexant Fed | | | (Suvorexant Fed/Suvorexant Fasted) | |
|---|---|---|---|---|---|---|---|---|
| | N | GM | 95% CI | N | GM | 95% CI | GMR | 90% CI |
| $AUC_{0-\infty}$ (µM · hr) | 12 | 13.2 | (10.60, 16.42) | 12 | 13.0 | (10.43, 16.16) | 0.98 | (0.90, 1.07) |
| $C_{max}$ (µM) | 13 | 1.0 | (0.79, 1.22) | 13 | 1.1 | (0.86, 1.34) | 1.09 | (0.90, 1.33) |

-continued

| Pharmacokinetic Parameter | Suvorexant Fasted | | | Suvorexant Fed | | | (Suvorexant Fed/ Suvorexant Fasted) | |
|---|---|---|---|---|---|---|---|---|
| | N | GM | 95% CI | N | GM | 95% CI | GMR | 90% CI |
| $T_{max}$ (hr) | 13 | 2.0 | 1.0, 4.0 | 13 | 3.0 | 1.0, 6.0 | 1.5 | (1.0, 3.0) |
| Apparent Terminal $t_{1/2}$ (hr) | 12 | 10.9 | 3.4 | 12 | 11.8 | 3.8 | — | — |

(GM: Geometric Mean, GMR: Geometric Mean ratio, CI: Confidence interval)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A pharmaceutical composition comprising:
   suvorexant in an amorphous form; and
   copovidone;
   wherein the pharmaceutical composition is prepared by a process comprising hot melt extrusion of a mixture comprising suvorexant and copovidone.

2. The pharmaceutical composition of claim 1, wherein the suvorexant is present in a form that contains at least 90 weight % of the amorphous form of suvorexant relative to other morphological forms of suvorexant.

3. The pharmaceutical composition of claim 1, wherein the suvorexant is present in a form that contains at least 95 weight % of the amorphous form of suvorexant relative to other morphological forms of suvorexant.

4. The pharmaceutical composition of claim 1, wherein the suvorexant is present in a form that contains at least 98 weight % of the amorphous form of suvorexant relative to other morphological forms of suvorexant.

5. The pharmaceutical composition of claim 1, wherein the suvorexant is present in a form that contains at least 99 weight % of the amorphous form of suvorexant relative to other morphological forms of suvorexant.

6. The pharmaceutical composition of claim 1, wherein the pharmaceutical composition additionally comprises lactose.

7. The pharmaceutical composition of claim 1, wherein the pharmaceutical composition additionally comprises microcrystalline cellulose.

8. The pharmaceutical composition of claim 1, wherein the pharmaceutical composition additionally comprises croscarmellose sodium.

9. The pharmaceutical composition of claim 1, wherein the pharmaceutical composition additionally comprises magnesium stearate.

10. A pharmaceutical composition comprising:
    suvorexant in an amorphous form;
    copovidone;
    lactose monohydrate;
    microcrystalline cellulose;
    croscarmellose sodium; and
    magnesium stearate;
    wherein the pharmaceutical composition is prepared by a process comprising hot melt extrusion of a mixture comprising suvorexant and copovidone.

11. The pharmaceutical composition of claim 10, wherein the suvorexant is present in a form that contains at least 90 weight % of the amorphous form of suvorexant relative to other morphological forms of suvorexant.

12. The pharmaceutical composition of claim 10, wherein the suvorexant is present in a form that contains at least 95 weight % of the amorphous form of suvorexant relative to other morphological forms of suvorexant.

13. The pharmaceutical composition of claim 10, wherein the suvorexant is present in a form that contains at least 98 weight % of the amorphous form of suvorexant relative to other morphological forms of suvorexant.

14. The pharmaceutical composition of claim 10, wherein the suvorexant is present in a form that contains at least 99 weight % of the amorphous form of suvorexant relative to other morphological forms of suvorexant.

15. The pharmaceutical composition of claim 11, which comprises 5 mg, 10 mg, 15 mg or 20 mg of suvorexant.

16. The pharmaceutical composition of claim 12, which comprises 5 mg, 10 mg, 15 mg or 20 mg of suvorexant.

17. The pharmaceutical composition of claim 13, which comprises 5 mg, 10 mg, 15 mg or 20 mg of suvorexant.

18. The pharmaceutical composition of claim 14, which comprises 5 mg, 10 mg, 15 mg or 20 mg of suvorexant.

* * * * *